(12) United States Patent
Escobar Valdes et al.

(10) Patent No.: US 8,586,027 B2
(45) Date of Patent: Nov. 19, 2013

(54) COMPOSITION TO OBTAIN A BIOLOGICAL FUNGICIDE AND BACTERICIDE WITHOUT THE USE OF ANTIBIOTICS TO CONTROL PLANT DISEASES ETC

(75) Inventors: Paulo Andrés Escobar Valdes, Talca (CL); Gustavo Adolfo Lobos Prats, San Javier (CL); Eduardo Patricio Donoso Cuevas, Talca (CL)

(73) Assignee: Bio Insumos Nativa Limitada, San Javier (CL)

( * ) Notice: Subject to any disclaimer, the term of this patent is extended or adjusted under 35 U.S.C. 154(b) by 0 days.

(21) Appl. No.: 13/261,019

(22) PCT Filed: Jun. 10, 2010

(86) PCT No.: PCT/CL2010/000021
§ 371 (c)(1),
(2), (4) Date: Mar. 26, 2012

(87) PCT Pub. No.: WO2010/142055
PCT Pub. Date: Dec. 16, 2010

(65) Prior Publication Data
US 2012/0183517 A1  Jul. 19, 2012

(30) Foreign Application Priority Data
Jun. 11, 2009 (CL) .................................. 1395-2009

(51) Int. Cl.
*A01N 63/00* (2006.01)
(52) U.S. Cl.
USPC ...................................................... 424/93.46

(58) Field of Classification Search
None
See application file for complete search history.

(56) References Cited

U.S. PATENT DOCUMENTS
6,524,998 B1 * 2/2003 Kloepper et al. ............. 504/100

FOREIGN PATENT DOCUMENTS
DE     102005056670 A1   5/2007

OTHER PUBLICATIONS

Seddon et al., Disease Control with Bacillus brevis: Update and Future Prospects, Modern Fungicides and Antifungal Compounds V, 2007, pp. 253-262.*
Xu et al., Phylogenetic relationships between Bacillus species and related genera inferred from comparison of 3' end 16S rDNA and 5' end 16S-23S ITS nucleotide sequences, International Journal of Systematic and Evolutionary Microbiology (2003), 53, 695-704.*

* cited by examiner

*Primary Examiner* — Suzanne M Noakes
*Assistant Examiner* — Stephen Chong
(74) *Attorney, Agent, or Firm* — Edward D. Robinson; TechLaw LLP

(57) ABSTRACT

A composition used to obtain a biological fungicide and bactericide without the use of antibiotics to control plant diseases, consisting in native strains. The composition is characterized in that it includes strains of the bio-controllers *Bacillus* spp and *Brevibacillus parabrevis* in a concentration of ten to the power of eight spores/g at a ratio of 1:1:1:1 for each of the strains, with a broad-spectrum action on phytopathogenic bacteria and late blight.

3 Claims, 3 Drawing Sheets

| Category | Damage Level in the Clusters |
|---|---|
| 0 | No infected grapes |
| 1 | One or two infected grapes |
| 2 | Three to five infected grapes |
| 3 | Over five grapes infected. |

| Treatments | Severity |
|---|---|
| T1 | 0.43 |
| T2 | 0.67 |
| T3 | 1.23 |
| T4 | 1.4 |

COMPOSITION TO OBTAIN A BIOLOGICAL FUNGICIDE AND BACTERICIDE WITHOUT THE USE OF ANTIBIOTICS TO CONTROL PLANT DISEASES ETC

BACKGROUND OF THE INVENTION

The invention that is hereby applying for claiming a patent refers to a composition to obtain a biological fungicide and bactericide to control plant diseases, consisting of native strains of *Bacillus* spp and *Brevibacillus parabrevis* biocontrollers in a concentration of 108 spores/g, at the ratio of 1:1:1:1, with a broad-spectrum action on phytopathogenic bacteria and late blight caused by *Phytophthora infestans*.

The invention composition permits to control bacterial and fungal diseases without the use of antibiotics or cupric compounds, and given its characteristics it does not present any environmental restriction and may be used in organic production.

Regarding the state of the art we can cite the invention patent ES No 2,307,870, which describes a composition containing two or more *trichoderma* species, in their natural state or genetically modified through radioactive methods or otherwise, original strains of natural or laboratory *Trichoderma* species and/or subspecies, to which a total hydro-alcoholic extract of a *Rubus* species, or some of its components, is added in a mixture of natural or chemical substances destined to obtain bacteriostatic bactericide and/or a preservative; where such composition is:

a) A composition created on the basis of two or more *Trichoderma* strains by adding any synthetic, organic or inorganic substance, including preservatives and drivers of these substances, destined to give a bactericidal bacteriostatic characteristic, and/or any fungal substance in lower doses than those necessary to destruct the *Trichoderma* culture, or fungicide substances to which the selected *Trichoderma* species are immune, but sufficiently strong to give a fungal character to such preparation, as well as the addition of substances of any origin and nature, and/or instillers of the bactericidal bacteriostatic action (including penicillin as an impure extract of the driving fungus and/or of commercial origin, macrolides, neo-macrolides, cyclosporine, and any other therapeutic family of a bactericidal bacteriostatic fungicide.

b) A composition created on the basis of two or more alive and active *Trichoderma* species that due to their antagonist character must have a separate commercial presentation, but must be mixed at the time when they are going to be used or in a period of time not exceeding 45 days after applying the first species, all this in order to reach a broader spectrum of action than that given by any species and of any possible origin in any vegetative growth phase, that could or could not contain agents giving them the additional properties as bacteriostatic bactericide.

In addition, it refers to a formulation of a broad-spectrum bactericidal bacteriostatic fungicide acting on fungi and/or bacteria that are responsible for fungal diseases and/or bacteriosis in human beings and/or animals, and on bacteriosis and/or fungi that may infect food, thereby preventing their growth, and/or in the healing phase on already installed bacteria and/or fungi, used in the preventive and/or healing phase, and consisting of a commercial presentation for pastry permitting to introduce one or more alive *Trichoderma* strains and/or an extract thereof, with lactones as active principle, into a sufficient concentration to permit the inhibition of fungal growth (for example, penicillin and other) over cooked bread in particular and over cooked dough in general, thus extending its useful life.

Another invention patent is ES No 2,246,834 and refers amply to the plant growth and development field, particularly to procedures and compositions to improve growth and resistance to plant diseases. The invention refers to the initiation and promotion of plant growth using a combination of multiple biological control strategies on the soil or on a growing medium without soil to control nematodes and foliar pathogens.

The invention also refers to a new composition of a plant growth medium comprising of chitin and non-chitinolytic plant-growth promoting rhizobacteria (PGPR) that create growth synergy and resistance to plant diseases. Additionally, the invention refers to a new synergic procedure to be used either in a seed treatment or in the application of a composition of a cultivation medium without soil formed by a chitinous element and bacterial elements for the preparation and development of plants and transplants.

Additionally, a composition is provided that consists of at least two PGPR bacteria strains and a chitinous compound selected among chitin, chitin in flakes, chitosana and precursors thereof, in an interval of 0.1% to 10.0% or a compound with an equivalent effect. The plant-growth promoting rhizobacteria (PGPR) consist at least of one bacterial strain that may induce a systemic resistance in the plant against vegetable diseases. The composition consists also of a chitinous: a compound that may have a control activity on nematodes. In one embodiment, at least one of the PGPR bacterial strains is not chitinolytic. The chitinous compound is preferably an organic amine or otherwise an amino polysaccharide.

The purpose of this invention is to provide a biological fungicide and bactericide composition destined to control cultivated plant diseases, such as bacterial cancer in stone fruits (*Pseudomonas syringae* pv. *syringae*); bacterial speck of tomato (*Pseudomonas syringae* pv. *tomato*); bacterial spot of tomato (*Xanthomonas campestris* pv. *vesicatoria*), bacterial blight of the European Hazelnut (*Xanthomonas campestris* pv. *coralina*), Black walnut blight (*Xanthomonas juglandis*); Bacterial canker disease of tomato (*Clavibacter michiganensis* subsp. *michiganensis*), Acid rot (*Acetobacter* sp); soft rot (*Erwinia carotovora*) and Late Blight (*Phytophtora infestans*), but the composition has a wide range of disease control.

The composition is formed in similar proportions by bacterial strain of the *Brevibacillus parabrevis* type No. 4; *Bacillus subtilis* strain No. 5; *Bacillus cereus* strain No. 6 and *Bacillus cereus* strain No. 7.

This composition permits to control bacterial and fungal diseases in cultivated plants, without the use of antibiotics or copper compounds and do not present environmental restrictions and may be used in the organic production, which is not the case of the fungicides available at present.

DESCRIPTION OF THE DRAWINGS

To prove the results and incidence obtained with the use or application in cultivated plants, using the composition obtained with the above-mentioned bacterial strains, we will do it partially based on the drawings that form an integral part of the invention, where.

Figure 1:
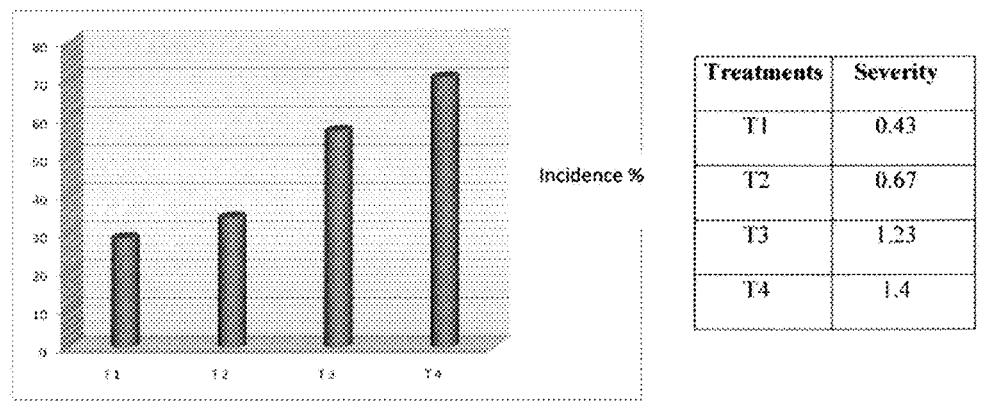
FIG. 1. Shows a graph with the acid rot incidence in *Vitis viniftra* L. cv. Syrah, in clusters treated with the invention composition. the biocontroller (Nacillus Pro) T1; Nacillus Pro+Chemical treatment (Switch+BC 1000) T2; Chemical treatment (Switch+BC 1000) T3; Core sample T4. Season 2006-2007. Evaluation Nov. 4, 2007. Columns having the same letter do not statistically differ according to the Tukey test (p<0.01).
Figure 2:
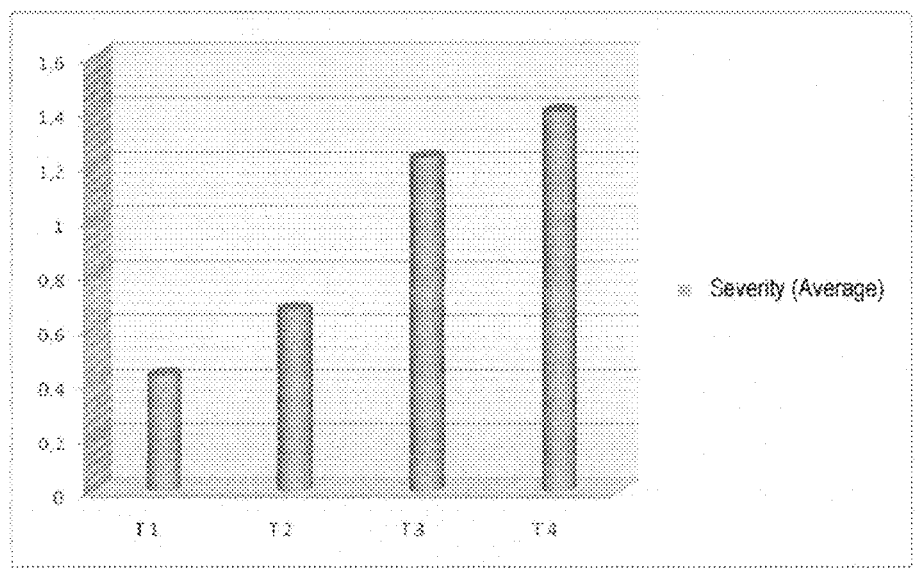
FIG. 2. Shows a graph with a severe acid rot in *Vitis vinNra* L. cv. Syrah, in groups treated with the biocontroller Nacillus Pro T1; Nacillus Pro+Chemical treatment (Switch+BC 1000) T2; Chemical treatment (Switch+BC 1000) T3; Testigo T4. Season 2006-2007. Evaluation Nov. 4, 2007. The columns with the same letter do not statistically differ according to Tukey's test (p<0.01).

DETERMINATION OF THE MINIMUM INHIBITORY CONCENTRATIONS (MIC) OF STRAINS WITH AN INHIBITORY CAPACITY

For each EFB strain (Endospore-Forming Bacteria corresponding to bio-controlling strains), a tube was inoculated with 6 ml of nutrition broth (NB) with the colony obtained from a pure culture, which was let grow under constant agitation for 24 hours at 20° C.

For the phythopatogenic bacteria, a colony of the agar plate was taken with the inoculation loop and inoculated in a flask with 200 ml of the BN liquid culture media, and let it grow under constant agitation for 24 hours at 20° C.

On Petri dishes with 30 ml of nutrient agar, one ml of the pathogen bacteria culture was added, which was homogeneously distributed on the plate. The excess was removed after 30 minutes.

Once the pathogen excess was removed, orifices were made in the agar with a punch of 0.5 cm. in a number of 9 per Petri dish. In each of these dishes, 50 µl of the strain culture of biocontrollers were added to the following concentrations: $1*10P^{8P}$, $1*10P^{7P}$, $1*10P^{6P}$, $1*10P^{5P}$, $1*10P^{4P}$, $1*10P^{3P}$ and $1*10P^{2P}$ CFU/ml.

The dishes with the pathogen and the EFB strains were kept at 4° C. for two hours, and then incubated at 25° C., and the presence of inhibition halos was seen until 72 hours after inoculation.

For each combination of pathogenic bacteria EFB strain, three repetitions were used, including also control plates only with the pathogenic bacteria and the Bs strain. In this way, the EFB strain was selected producing a significant inhibition halo around the orifices were they had been sown and their presence was consistent in the repetitions.

The measurement consisted in the diameter of the inhibition halo formed by each strain, in each one of the dilutions used, and it was considered also as an inhibition expression on the pathogen.

The results are shown in Table 1, indicating the minimum concentrations at which each strain shows an inhibitory activity on the different pathogens. It is interesting to note that the strain showed minimum concentrations, similar to pathogens, of the same gender, and there were no differences in the control capacity on different pathovars and even on different species.

TABLE 1

MINIMUM INHIBITORY CONCENTRATIONS (CFU/ML), REACHED BY 4 EFB STRAINS ON PHYTOPATHOGENIC BACTERIA

| Strain | Pathogen | | | | | |
|---|---|---|---|---|---|---|
| | *Clavibacter michiganensis* subsp. *michiganensis* | *Xanthomonas campestris* pv. Vesicatoria | *Xanthomonas campestris* pv. Corylina | *Xanthomonas juglandis* | *Pseudomonas syringae* pv. tomato | *Pseudomonas syringae* pv. syringae |
| *Brevibacillus parabrevis* strain N4 | $10^6$ a | $10^6$ a | $10^6$ a | $10^6$ a | $10^6$ a | $10P^4$ |
| *Bacillus subtilis* strain N5 | $10^6$ a | $10^5$ b | $0^5$ b | $10^5$ b | $10^5$ b | $10^5$ b |
| *Bacillus cereus* strain N6 | $10^5$ b | $10^3$ c | $10^3$ c | $10^3$ c | $10^3$ c | $10^3$ c |
| *Bacillus cereus* strain N7 | $10^5$ b | $10^2$ d | $10^2$ d | $10^2$ d | $10^4$ c | $10^4$ c |

Determination of Compatibility Among Native EFB Strain for the Control of Diseases Using the same methodology as in assay 1, all mixtures of the 4 EFB strains were evaluated by pathogen and then compared in their inhibition to individual strains.

TABLE 2

INHIBITORY HALO DIAMETER OF 4 EFB STRAINS AND THEIR COMBINATION OVER 6 PHYTOPATHOGENIC BACTERIA

| Strain | *Clavibacter michiganensis* subsp. *michiganensis* | *Xanthomonas campestris* pv. vesicatoria | *Xanthomonas campestris* pv. Corylina | *Xanthomonas juglandis* | *Pseudomonas syringae* pv. tomato | *Pseudomonas syringae* pv. syringae |
|---|---|---|---|---|---|---|
| 4 | 1.6 b | 2.6 b | 2.8 b | 2.7 b | 2.3 bc | 2.4 bc |
| 5 | 1.4 b | 2.8 b | 2.4 b | 3.1 b | 3.2 b | 2.9 b |
| 6 | 1.5 b | 2.3 b | 2.1 b | 2.5 bc | 1.5 c | 1.4 c |

TABLE 2-continued

INHIBITORY HALO DIAMETER OF 4 EFB STRAINS AND THEIR
COMBINATION OVER 6 PHYTOPATHOGENIC BACTERIA

| Strain | Clavibacter michiganensis subsp. michiganensis | Xanthomonas campestris pv. vesicatoria | Xanthomonas campestris pv. Corylina | Xanthomonas juglandis | Pseudomonas syringae pv. tomato | Pseudomonas syringae pv. syringae |
|---|---|---|---|---|---|---|
| 7 | 2.1 b | 1.4 c | 1.5 c | 1.6 c | 1.8 c | 1.9 bc |
| MIXTURE | 6.4 a | 6.9 a | 7.1 a | 7.2 a | 6.4 a | 6.5 a |

Determination of the Control Capacity of EFB Strains Based on Competition

On the Petri dishes, with nutrient agar, the pathogen under study was sown, forming 5.5-cm long parallel lines, in four lines per plate. Perpendicularly on one of the sides of these lines, the EFB were sown also on a line, and thereafter the plates were set to incubate at 26° C. for 7 days, after which both the pathogen inhibition and the growth level that the EFB strain were able to cause on the pathogen were measured, which was evaluated in the form of a percentage of the pathogen line covered or inhibited by the EFB strain, and then these data were submitted to a variance analysis and, if significant, to a media separation test. 12 repetitions were used per treatment.

The control treatment consisted of non-treated inoculated plants, a treatment based on the available chemical alternative, which was also executed with 4 applications at the above-mentioned times and with the dose recommended in their label, and additionally some plants were left without inoculation and without application of the treatments in order to prove the inoculation efficacy.

Measurements were based on incidence (plant percentage with symptoms) and severity given by the percentage of plants with disease symptoms, for *Pseudomonas syringae* pv. *tomato*, percentage of wilted leaflets for *Clavibacter michiganensis* Subs. *michiganensis* and percentage of leaf area with bacterial speck, in the case of *Xanthomonas campestris* pv. *vesicatoria*.

TABLE 3

INHIBITORY HALO DIAMETER AND OVER GROWTH BY COMPETITION OF 4 EFB
STRAINS AND THEIR COMBINATION ON 6 PHYTOPATHOGENIC BACTERIA.

| | Clavibacter michiganensis subsp. michiganensis | | Xanthomonas campestris pv. vesicatoria | | Xanthomonas campestris pv. corylina | | Xanthomonas juglandis | | Pseudomonas syringae pv. tomato | | Pseudomonas syringae pv. syringae | |
|---|---|---|---|---|---|---|---|---|---|---|---|---|
| Strain | I mm | C mm | I mm | C mm | I mm | C mm | I mm | C mm | I mm | C mm | I mm | C mm |
| Brevibacillus parabrevis Strain N4 | 1.6 | 4.8 | 2.6 | 31.2 | 2.8 | 5.6 | 2.7 | 3.24 | 2.3 | 2.53 | 0.4 | 2.16 |
| Bacillus subtilis Strain N5 | 1.4 | 2.8 | 2.8 | 14 | 2.4 | 4.8 | 3.1 | 4.34 | 3.2 | 3.84 | 2.9 | 2.581 |
| Bacillus cereus Strain N6 | 1.5 | 4.5 | 2.3 | 52.9 | 2.1 | 71.4 | 2.5 | 70 | 1.5 | 36 | 1.4 | 47.6 |
| Bacillus cereus Strain N7 | 2.1 | 7.35 | 1.5 | 67.5 | 1.5 | 72 | 1.8 | 59.4 | 1.8 | 46.8 | 1.9 | 53.2 |

Live Evaluation in of the Bio-Controlling Capacity with the Invention Composition (Nacillus Pro.) in the Control of Bacterial Diseases in Tomato In 400-ml bags containing perlite substrate, organic soil and sand (1:2:1), tomato plants of the species *Maria Italia* with two true leaves were transplanted. One month alter transplantation, a group of plants was inoculated with *Clavibacter michiganense* subsp. *michiganense*, another with *Xanthomonas campestris* pv. *vesicatoria*, and the third one with *Pseudomonas syringae* pv. *tomato*, at a dose of 60 ml/plant with a concentration of $10P^{6P}$ bacteria/ml.

Each plant group was submitted to a manual inoculation. Treatments were executed with 2 applications prior to inoculation in flowerbed and then transplanted, and two applications at 5 and 10 days after the inoculation.

The assays took place independently in plant cultivation chamber at medium temperatures of 26° C. during the day and 20° C. during the night, and with 16 hours of light and 8 hours of darkness. Every 3 days after the applied treatments, observations were made to detect the presence of symptoms and signs until 40 days post inoculation.

Additionally strength parameters were measured, such as height and weight of the aerial and root portion.

The treatments for these assays were laid out in a completely random design with 5 replicates of 10 plants each per treatment.

T0: Absolute control
T1: Inoculation Control
T2: Nacillus Pro 3 g/l 4 applications.
T3: Chemical Control, Streptoplus 4 applications 120 g/100 l.

Results

In the case of *P. syringae* pv. *tomato*, the treatment with the invention composition (Nacillus Pro) reached a significant reduction both of the incidence and the severity, and differentiated both from the inoculated control treatment and the chemicals treatment, in terms of strength parameters, although higher height and weights were attained than those of the absolute control, only the inoculated control was statistically different. Something similar was observed in the *Clavibacter* control assay with an interesting effect on the severity variable where the treatment with Nacillus Pro reached a severity level that was statistically similar to the control without inoculation. In *Xanthomonas*, Nacillus Pro. continued to be the best treatment, both in terms of incidence and severity with a behavior similar to that observed in *Pseudomonas*, regarding the strength variables.

TABLE 4

EFFECT OF NACILLUS PRO, ON INCIDENCE, SEVERITY AND STRENGTH PARAMETERS OF TOMATO PLANTS ARTIFICIALLY INOCULATED WITH *P. SYRINGAE* PV. TOMATO.

| Treatment | Incidence (%) | Severity (%) | Height (cm) | Aerial dry weight (g) | Root dry weight (g) |
|---|---|---|---|---|---|
| T0: Absolute Control | 0 c | 0 c | 123 a | 37.3 ab | 6.4 ab |
| T1: Control with inoculation | 100 a | 73 a | 102 b | 30.1 b | 5.8 b |
| T2: Nacillus Pro 3 g/l | 34.4 b | 7.5 c | 132 a | 38.2 a | 6.8 a |
| T3: Chemical Control, Streptoplus | 86.7 a | 64 b | 105 b | 32.1 ab | 6.2 ab |

TABLE 5

EFFECT OF NACILLUS PRO, ON INCIDENCE, SEVERITY AND STRENGTH PARAMETERS OF TOMATO PLANTS ARTIFICIALLY INOCULATED WITH *C. MICHIGANENSIS* SUBS. *MICHIGANENSIS*.

| Treatment | Incidence (%) | Severity (%) | Height (cm) | Aerial dry weight (g) | Root dry weight (g) |
|---|---|---|---|---|---|
| T0: Absolute control | 0 d | 0 c | 123 a | 37.3 a | 6.4 ab |
| T1: Control with Inoculation | 100 a | 83.8 a | 98 b | 25.1 b | 4.1 b |
| T2: Nacillus Pro 3 g/l | 38.3 c | 8.5 c | 126 a | 32.72 a | 5.8 a |
| T3: Chemical Control, Streptoplus | 64.1 b | 54.4 b | 115 ab | 28.4 ab | 5.6 ab |

TABLE 6

EFFECT OF NACILLUS PRO, ON INCIDENCE, SEVERITY AND STRENGTH PARAMETERS OF TOMATO PLANTS ARTIFICIALLY INOCULATED WITH *X. CAMPESTRES* PV. *VESICATORIA*.

| Treatment | Incidence (%) | Severity (%) | Height (cm) | Aerial dry weight (g) | Root dry weight (g) |
|---|---|---|---|---|---|
| T0: Absolute control | 0 d | 0 d | 123 a | 37.3 a | 6.4 ab |
| T1: Control with Inoculation | 100 a | 83.8 a | 108 b | 29.2 b | 4.7 b |
| T2: Nacillus Pro 3 g/l | 18.3 c | 6.5 c | 129 a | 34.72 a | 5.9 a |
| T3: Chemical Control, Streptoplus | 64.1 b | 54.4 b | 117 ab | 27.4 ab | 5.3 ab |

Live Evaluation of the Biocontrolling Capacity of Nacillus Pro in the Control of Bacterial Diseases in Cherry and Pear Trees One-year old cherry tree plants of the Bin variety and pear tree plants of the Abate variety were transplanted into 4-1 bags containing perlite, organic soil and sand substrate (1:2: 1). One month after transplantation, a group of plants were inoculated with *Pseudomonas syringae* pv. *syringae*, at a dose of 60 ml/plant with a concentration of $10P^{6P}$ of bacteria/ml. The plants were sprayed before the leaves fell.

Treatments:

T0: Absolute control without inoculation and without applications

T1: Control with inoculation

T2: Nacillus Pro 1.5 g/l 5 applications, with the first being in February; two applications on the fall of leaves (5 and 80%), one in mid winter (the last week in July), one at sprouting start and the last when it was fully blossomed.

T3: Chemical control: Consisting of Nordox 60 g/100 l with 3 applications on the fall of leaves (5, 50 and 100%), two in mid winter and Streptoplus, at the sprouting and blossoming times at a dose of 60 g/100 l.

The assays took place on the experimental land of Bio Insumos Nativa Ltda.

The measurements consisted of incidence measured as a percentage of blighted buds.

The treatments for this assay were provided under fully random designs with 5 replicates of 10 plants each per treatment.

Results

In both fruit trees, the treatment with Nacillus Pro, could significantly reduce incidence of buds blighted by the pathogen. It even exceeded the standard chemical control.

TABLE 7

EFFECT OF NACILLUS PRO, ON INCIDENCE AND SEVERITY IN CHERRY TREE PLANTS AND PEAR TREE PLANTS ARTIFICIALLY INOCULATED WITH *P. SYRINGAE* PV. *SYRINGAE*.

| Treatment | Incidence in Cherry Trees (%) | Incidence in Pear Trees (%) |
|---|---|---|
| T0: Absolute Control | 0 c | 0 c |
| T1: Control with Inoculation | 64.3 a | 73 a |
| T2: Nacillus Pro | 24.4 c | 11.5 c |
| T3: Chemical Control | 46.7 b | 52.3 b |

Acid Rot Assay 3.1.1 Assay Location

This assay was located in Santa Cruz in the Province of Colchagua, Region VI, Chile, in the San Francisco land owned by Viña MontGras. Its geographic location is 34° 33' 18.48" South and 71° 23' 55.98" West; at an altitude of 153 meters.

3.2—Plant Material

The research took place during the 2006/2007 farming season, using wine grape of the Syrah variety as plant material. This was planted in 1997 and had been formed in rows, with a space between rows of 2.2 m. and distances over rows of 2.0 m. It presents drop irrigation system.

3.4.—Experimental Design

The assay was designed with blocks laid out randomly consisting on four treatments and three repetitions (three rows) of 50 plants each.

3.4.1.—Treatments

TABLE 8

TREATMENTS EVALUATED IN ACID ROT CONTROL OF WINE GRAPE CV. SYRAH SEASON 2006/2007.

| Treatment 1 | Nacillus Pro ® |
|---|---|
| Treatment 2 | Nacillus Pro ®. + orchard treatment (Switch (Cyprodinil + Fludioxonil) and BC 1000 (Extract of grapefruit seed and pulp (organic acids plus Bioflavonoids)) only in the presence of disease symptoms. |
| Treatment 3 | Orchard treatment (Switch (Cyprodinil + Fludioxonil) and BC 1000 (Extract of grapefruit seed and pulp (organic acids plus Bioflavonoids)) only in the presence of the disease. |
| Treatment 4 | Core sample |

T1: Two applications of Nacillus Pro. (3 kg/ha) last week in January and first week in February; cluster tightening and golden red ripening respectively; and a pre-harvest application on the third week of March.

T2: Switch application (1 kg/ha) last week of January and first week of February, cluster tightening and golden red ripening respectively and three pre-harvest applications of BC 1000 (20 Kg/ha) during the third and fourth week in March and first week in April.

T3: Two applications of Nacillus Pro (3 Kg/ha) and Switch (1 Kg/ha) in the last week of January and first week of February, cluster tightening and golden red ripening. A pre-harvest Nacillus Pro®. application (3 Kg/ha), during the third week in March and three pre-harvest applications of BC 1000 (20 Kg/ha) during the third and fourth week of March and first week in April.

T4: Sample core. No applications.

3.5.—Sample Collection and Analysis

The measurement took place five days before harvesting, 50 plants were harvested per repetition. Incidence was measured as a percentage of affected fruits within the total fruits of each repetition and the severity was measured according to a scale and number of infected grapes per cluster.

TABLE 9

SCALE USED TO MEASURE SEVERITY OF ACID ROT IN WINE GRAPE CV. SYRAH SEASON 2006/2007.

| Category | Level of Damage in the cluster |
|---|---|
| 0 | Without infected grapes |
| 1 | One or two infected grapes. |
| 2 | Three to five infected grapes. |
| 3 | Over five infected grapes. |

4.1.—Evaluation of Acid Rot Incidence in Different Treatments Applied in the Orchard.

The results obtained in this assay led to determine which level of incidence presents this disease in the orchard and then led to clearly define the most effective treatment.

Based on the data obtained in the ANOVA, which gave highly significant differences, the separation of media was executed through the Tukey method (HSD). Based on this result it was determined that the best treatment was Nacillus Pro and Nacillus Pro associated to chemical control proving that the bio-controlling action of this bacteria is effective with incidence percentages of 28.6% and 34.0%, respectively. The chemical treatment (orchard treatment) on its own was not effective to prevent and control acid rot, as its incidence percentage was 56.6%, whereas the sample core was 70.6% with both being statistically similar.

4.2.—Evaluation of Acid Rot Severity in the Different Treatments Applied in the Orchard.

| Category | Damage Level in the cluster |
|---|---|
| 0 | No grapes infected |
| 1 | One or two grapes infected. |
| 2 | Three to five grapes infected. |
| 3 | Over five grapes infected. |

| Treatments | Severity |
|---|---|
| T1 | 0.43 |
| T2 | 0.67 |
| T3 | 1.23 |
| T4 | 1.4 |

Table 4.2 confirms that Nacillus Pro biocontroller does not only reduce the appearance of the disease in the vineyard, but also its attack is weaker, as the severity is clearly lower with values of 0.43 in T1; 0.67 in T2; 1.23 in T3; 1.40 in T4. Highly significant differences were observed between the proposed treatment with "Nacillus Pro" and the chemical treatment used in the orchard where the assay took place.

According to the foregoing, the Nacillus Pro product has a biocontrolling effect on the agents that cause acid rot in *Vitis vinifera* L. cv. Syrah. Thus, the use of this microbial antagonist formulation as biocontroller agent would permit to reduce the use of chemicals and thereby help to delay the risk of developing strains that are resistant to pathogens in this field (Gullino et al, 1995). This is one of the main advantages of the plant pathogen biological control which has created the current interest of scientists in looking for new alternatives regarding antagonist microorganisms.

Control Assays of *Pseudomonas syringae* pv. *syringae* in Pear Trees

The purpose of this assay was to define the controlling action of the invention composition (Nacillus pro.) on the flower blight in pear trees caused by *Pseudomonas syringae* pv. *syringae*. For this purpose, two assays were executed in the city of Longavi.

Methodology

Orchard planted with the Abate Fetel variety, with high incidence and severity in previous seasons.

Treatments:
    T1: Control without applications
    T2: Orchard handling (3 Streptoplus+3 Citocur)
    T3: Combined handling (3 Streptoplus+3 Nacillus)
    T4: Biological handling: (4 Nacillus Pro).

Dose:
    Streptomycin: 60 g/100 l of P.C.
    Copper sulphate: 1.5 Kg./10001 water/ha.
    Nacillus Pro: 2.4 Kg/1200 l water/ha.

Each treatment consisted of 5 repetitions, each formed by 10 plants in a design of random blocks.

Results

Figure 5:
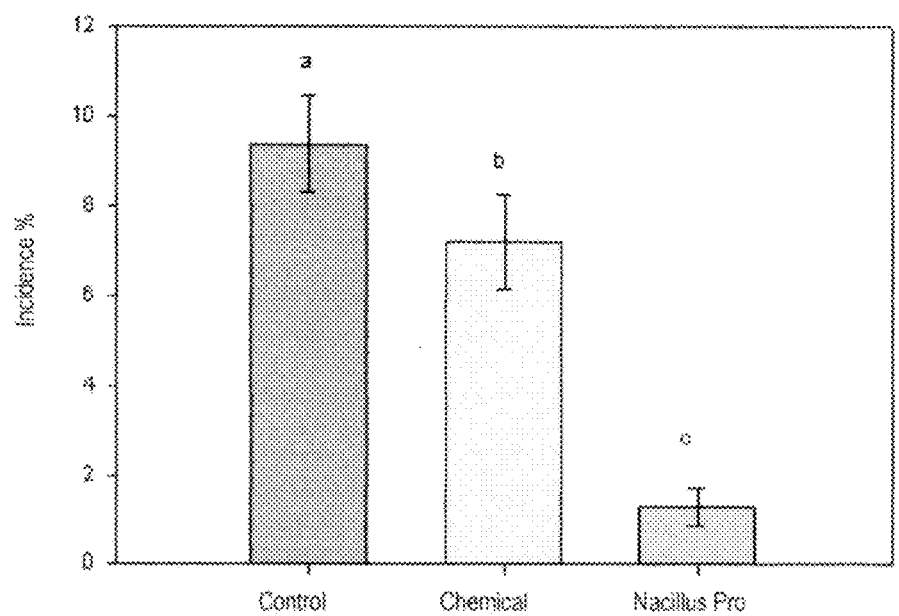
FIG. 5. Shows the damage incidence in Abate flower buds under different handling of *Pseudomonas* control.

The plants presented symptoms as shown in FIG. 5, all treatments were differentiated from the control treatment and the treatments with presence of the composition of the Nacillus Pro invention, were the ones that presented the lowest level of damage. And the treatment with Nacillus Pro presented the lowest percentage of affected trees and was statistically differentiated from the purely chemical handling.

The damage percentage was 8% in the control treatment, and it only statistically differed from the treatments that included the application of Nacillus Pro. Thus it can be inferred that while the chemical handling did not differ from the control, the Nacillus Pro application, with or without antibiotics, showed a level of damage statistically lower than the control and only the Nacillus Pro, in an isolated way, showed different results from the chemical handling, indicating a level of incompatibility of Nacillus Pro with antibiotics.

Figure 3:
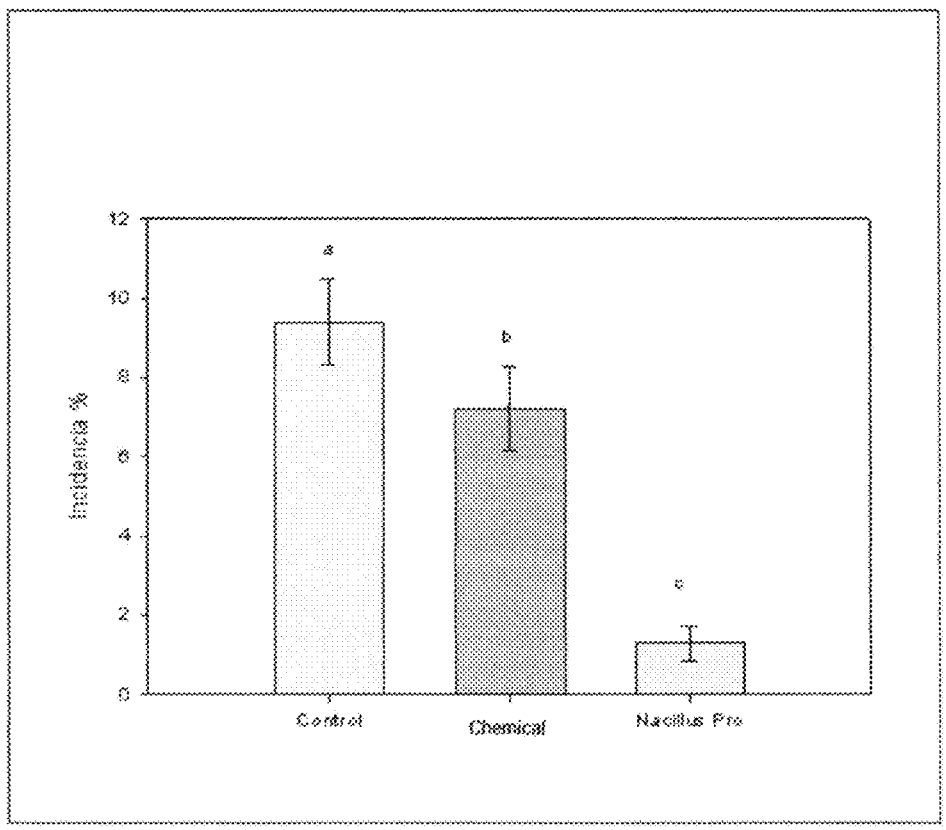
FIG. 3. Shows the incidence percentage of damage in Abate pear-tree shoots, under different control handling of *Pseudomonas*.
Figure 4:
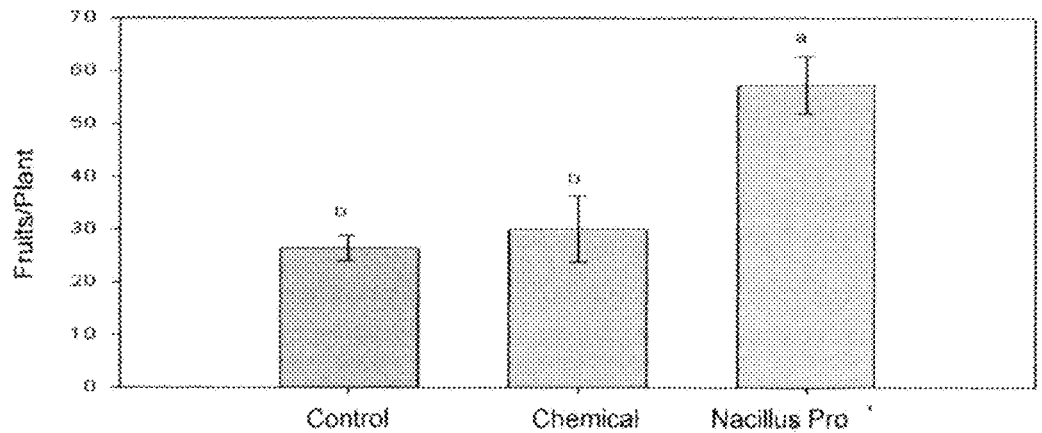
FIG. 4. S fruits per Abate pear plants, under different handling of *Pseudomonas* control.

Regarding the percentage and of fruit setting and fruits per tree, the only treatments that were different from the control were those including the Nacillus Pro product, and the treatment with only Nacillus Pro was better than the chemical handling. See FIGS. 3 and 4.

DESCRIPTION OF THE INVENTION

A biological fungicide and bactericide composition destined to control illnesses in cultivated plants, such as bacterial cancer in stone fruits (*Pseudomonas syringae* pv. *syringae*); bacterial speck of tomato (*Pseudomonas syringae* pv. *tomato*); bacterial spot of tomato (*Xanthomonas campestris* pv. *vesicatoria*), Bacterial blight of the European Hazelnut (*Xanthomonas campestris* pv. *coralina*) Black Walnut blight (*Xanthomonas juglandis*); Bacterial Canker of tomato (*Clavibacter michiganensis* subsp. *michiganensis*), Acid rot (*Acetobacter* sp); soft rot (*Erwinia carotovora*) and Late Blight (*Phytophtora infestans*), but the composition has a wide range of disease control. The composition is formed by bacteria, *Brevibacillus parabrevis* strain No. 4; *Bacillus subtilis* strain No. 5; *Bacillus cereus* strain No. 6 and *Bacillus cereus* strain No. 7. The composition includes a ratio of weight of the mixture of strains of 0.01% to 30%.

EXAMPLES OF EMBODIMENTS

Example 1

From 0.25% to 25% of Bacteria, *Brevibacillus parabrevis* strain No. 4; from 0.25% to 25% p/p of *Bacillus subtilis* strain No. 5; from 0.25% to 25% p/p *Bacillus cereus* strain No. 6 and from 0.25% to 25% p/p *Bacillus cereus* strain No. 7.

The invention claimed is:

1. An agricultural bactericide composition lacking antibiotics for controlling plant diseases, comprised of native strains, wherein the composition comprises biocontroller strains *Brevibacillus parabrevis* NRRL B-50390; *Bacillus subtilis* NRRL B-50391; *Bacillus cereus* NRRL B-50392; and *Bacillus cereus* NRRL B-50393 in a concentration of $10^8$ spores/g, at a ratio of 1:1:1:1, for each of the strains, with an ample spectrum on phytopathogenic bacteria.

2. The agricultural bactericide composition of claim 1, further comprising zeolite as a carrier.

3. The agricultural bactericide composition of claim 1, wherein the weight ratio of strains being 0.01% to 30%, wherein the ratio is in a w/w dry weight basis.

* * * * *